US008110519B2

(12) United States Patent
Kobayashi et al.

(10) Patent No.: US 8,110,519 B2
(45) Date of Patent: Feb. 7, 2012

(54) POLYMER-SUPPORTED METAL CLUSTER COMPOSITION

(75) Inventors: Shu Kobayashi, Tokyo (JP); Kuniaki Okamoto, Tokorozawa (JP); Ryo Akiyama, Tokyo (JP); Keiji Ohno, Sakado (JP); Yoshio Inagaki, Isehara (JP)

(73) Assignees: Japan Science & Technology Agency, Saitama (JP); Wako Pure Chemical Industries, Ltd., Osaka (JP); Fuji Photo Film Co., Ltd., Kanagawa (JP); Shu Kobayashi, Tokyo (JP)

( * ) Notice: Subject to any disclaimer, the term of this patent is extended or adjusted under 35 U.S.C. 154(b) by 1552 days.

(21) Appl. No.: 10/590,206

(22) PCT Filed: Mar. 7, 2005

(86) PCT No.: PCT/JP2005/003848
§ 371 (c)(1),
(2), (4) Date: Aug. 22, 2006

(87) PCT Pub. No.: WO2005/085307
PCT Pub. Date: Sep. 15, 2005

(65) Prior Publication Data
US 2008/0058200 A1     Mar. 6, 2008

(30) Foreign Application Priority Data

Mar. 8, 2004   (JP) ................. 2004-064520

(51) Int. Cl.
*B01J 31/06*   (2006.01)
*B01J 31/00*   (2006.01)
*B01J 31/16*   (2006.01)
*B01J 31/22*   (2006.01)
*B01J 23/40*   (2006.01)
*B01J 23/42*   (2006.01)
*B01J 23/44*   (2006.01)
*B01J 23/46*   (2006.01)
*B01J 23/52*   (2006.01)
*B01J 23/75*   (2006.01)
*B01J 23/755*  (2006.01)

(52) U.S. Cl. ........ 502/159; 502/150; 502/325; 502/326; 502/337; 502/339

(58) Field of Classification Search .................. 502/150, 502/159, 325, 326, 337, 339
See application file for complete search history.

(56) References Cited

FOREIGN PATENT DOCUMENTS
EP       1366814 A       12/2002
(Continued)

OTHER PUBLICATIONS

Toshima et al., "Substrate selectivity by the polymer support in hydrogenation . . . ", Reactive Polymers 15 (1991) 135-145.
(Continued)

*Primary Examiner* — Stuart Hendrickson
*Assistant Examiner* — Daniel Berns
(74) *Attorney, Agent, or Firm* — Jenkins, Wilson, Taylor & Hunt, P.A.

(57) ABSTRACT

The objective is to present compositions obtained by supporting by polymers micro clusters of transition metals and the like that are useful as catalysts in various reactions and, once used, are readily recovered and reused.
A polymer-supported metal cluster composition is obtained by supporting a transition metal by a cross-linked polymer, and the polymer-supported cluster composition is characterized by the cross-linked polymer obtained by cross-linking of a cross-linkable polymer containing a hydrophilic side chain and a hydrophobic side chain group having a cross-linkable functional group. This polymer-supported metal cluster composition is, for example, preferably formed by first forming a micelle composed of the metal clusters supported by the cross-linkable polymer in a suitable solution and subsequently subjecting the cross-linkable polymer to a cross-linking reaction. The composition is useful as a catalyst and the like in hydrogenation reactions, dehydrogenation reactions, allylic substitution reactions, oxidation reactions, coupling reactions and carbonylation reactions.

12 Claims, 1 Drawing Sheet

FOREIGN PATENT DOCUMENTS

| | | | |
|---|---|---|---|
| EP | 1537913 A | 6/2006 | |
| JP | 6-15184 | 1/1994 | |
| JP | 2003-510167 | 3/2003 | |
| WO | 02/066158 | 8/2002 | |
| WO | 02/072259 | 9/2002 | |
| WO | 02/072644 | 9/2002 | |
| WO | WO2004/024323 | 3/2004 | |
| WO | WO2005/085307 | 9/2005 | |

OTHER PUBLICATIONS

Akiyama et al., "The Polymer Incarcerated Method for the Preparation of Highly Active Heterogeneous Palladium Catalysts", JACS 2003, 125, 3412-3413.

Zecca et al., "Metal palladium supported on amphiphilic microporous synthetic organic supports", J. Molecular Catalysis A: Chemical 129 (1998) 27-34.

Miyamura et al., "Polymer-micelle incarcerated ruthenium catalyts for oxidation of alcohols and sulfides", Tetrahedron 61 (2005) 12177-12185.

International Preliminary Report on Patentability corresponding to International Patent Application No. PCT/JP2005/003848 dated Nov. 29, 2006.

International Search Report corresponding to International Patent Application No. PCT/JP2005/003848 dated Jun. 7, 2005.

Klingelhöfer et al., "Preparation of Palladium Colloids in Block Copolymer Micelles and Their Use for the Catalysis of the Heck Reaction," Journal of the American Chemical Society. vol. 119, No. 42 pp. 10116-10120 (1997).

Official Action corresponding to European Patent Application No. 05 720 120.4-2104 dated Feb. 18, 2009.

Supplementary European Search Report corresponding to European Patent Application No. 05720120.4-2104 dated Dec. 9, 2008.

POLYMER-SUPPORTED METAL CLUSTER COMPOSITION

FIELD OF THE INVENTION

The present invention relates to a composition obtained by stabilizing transition metal clusters such as those of palladium and the like on an amphiphilic polymer to obtain a form that can be recovered without the metal clusters leaching, to maintain its catalytic function, to be immobilized on a carrier and to be bonded into a network.

PRIOR ART

Attempts have been made for many years to use metal polymer composite materials immobilizing various metals on a variety of carriers as catalysts. Many of them utilized ligands bonded to nitrogen and phosphorus atoms, and problems were associated with their usage. For example, the catalytic activity was generally insufficient, and the activity declined gradually due to leaching of the metal when the composite materials were recovered and reused.

Catalyst compositions obtained by supporting metal catalysts by polymers using micro encapsulation were recently developed, but these compositions encountered the problem of leaching of the supported metal depending on the type of reactions involved. (Reference 1)

In addition, methods to immobilize metal catalysts as metal clusters on a carrier surface were developed, but the problem was that the catalytic activity achieved was highly dependent on the cluster size and the activity declined as the cluster size increased.

The use of micro metal clusters supported by polymer micelles as catalysts was recently reported. However, stability thereof was insufficient and it was difficult to recover and reuse, since such metal-polymer micelle composite materials are present as colloidal solutions. (Reference 2)

Reference 1: WO2004/024323.
Reference 2: J. Am. Chem. Soc., 1997, 119,10116.

PROBLEMS TO BE SOLVED BY THE INVENTION

The objective of the present invention is to present compositions obtained by supporting by polymers micro clusters of transition metals and the like, which are useful as catalysts in various reactions and, once used, are readily recovered and reused.

MEANS TO SOLVE THE PROBLEMS

The inventors discovered that the problems described above could be solved by using a polymer having a specific structure, that is, a polymer wherein a hydrophobic side chain (for example, aromatic groups and the like) and a hydrophilic and cross-linkable side chain are directly bonded to a main chain thereof, thus the inventors completed the present invention. By using such a polymer, a micelle can readily be formed in a liquid phase. As a result, the metal is stabilized and supported (incarcerated or immobilized) in the form of micro clusters by the polymer due to an interaction, for example, with the aromatic ring of the aromatic group present in the hydrophobic side chain of the polymer, and can exhibit excellent catalytic activity. As this micelle contains cross-linkable functional groups, the micelle can be allowed to react with a carrier such as beads, substrates and the like made of resin, glass and the like or to react with other micelles. As a result, this metal cluster composition can be immobilized on a carrier, and micelles of the metal cluster composition can take the structure of numerous three-dimensionally connected networks. Since the composition has such structure, problems of the leaching of the metal clusters depending on the reaction type can be eliminated and the re-utilization efficiency can be improved. As the micelles can also be molded into a film, it becomes possible to manufacture a functional film and the like containing dispersed micro metal clusters.

That is, the present invention is a polymer-supported metal cluster composition comprising a transition metal and a cross-linked polymer, wherein the transition metal is supported by the cross-linked polymer and the cross-linked polymer is obtained by cross-linking a cross-linkable polymer containing a hydrophobic side chain, such as an aromatic group, and a hydrophilic side chain having a cross-linkable functional group, and the metal clusters is 20 or smaller in diameter.

This polymer-supported metal cluster composition is preferably prepared, in a solution, by forming a micelle wherein clusters of the metal are supported (incarcerated of immobilized) by the cross-linkable polymer and then cross-linking the cross-linkable polymer.

Furthermore, the present invention includes the use of the above composition for a catalyst in a hydrogenation reaction, an oxidation reaction, a dehydrogenation reaction, an allylic substitution reaction, a coupling reaction, such as Heck, Suzuki, Stille, Hiyama, Negishi, Sonogashira and Buchwald-Hartwig reactions and a coupling reaction using a Grignard reagent, or a carbonylation reaction.

Effect of the Invention

The inventors successfully developed a polymer-supported metal cluster composition, which is insoluble in any type of solvents and can easily be recovered and reused without leaching of the supported metal clusters. This composition was made by first supporting a metal by a polymer micelle as described above containing cross-linkable functional groups and allowing the micelle to agglomerate and subsequently cross-link. In addition, the inventors also succeeded in immobilizing the metal-containing polymer micelle prepared on carriers such as glass on which polymer micelles were difficult to immobilize previously. The polymer-supported metal cluster composition of the present invention was found to have an extraordinary high catalytic activity, since the supported metal is stabilized as micro clusters in the micelle. In addition, the polymer-supported metal cluster composition of the present invention has potential applications as a manufacturing raw material for electrodes, selective adsorption filters, molecular sieve filters, adsorption agents, hydrogen storage agents, semiconductors and the like in addition to its applications as a catalyst and in functional films.

DETAILED DESCRIPTION OF THE INVENTION

The cluster composition of the present invention has a structure wherein the metal is supported as micro clusters in(on) a polymer micelle due to the interaction with the polymer.

As the metal, Group 8 transition metals such as iron, ruthenium, osmium and the like, Group 9 transition metals such as cobalt, rhodium, iridium and the like, Group 10 transition metals such as nickel, palladium, platinum and the like, Group 11 transition metals such as copper, silver, gold and the like and Group 12 transition metals such as zinc, cadmium, mercury and the like may be cited. Of these, palladium, cobalt, nickel, rhodium, ruthenium, iridium, gold, platinum and the like are preferred, palladium, ruthenium, iridium, gold, platinum and the like are more preferred and palladium, platinum and the like are particularly preferred.

Now, these transition metals may be supported in a combination of at least two.

In addition, a metal with zero valence is preferred.

The method to make the metal supported by a polymer is not particularly restricted, but, for example, is performed as mentioned below. A polymer having the structure described above and a metal precursor are (a) dissolved in a suitable polar good solvent to form a metal-supported micelle and subsequently agglomerated using a suitable polar poor solvent, (b) dissolved in a suitable non-polar good solvent to which a suitable polar solvent is subsequently added to form a metal-supported micelle, and a polar poor solvent is further added to agglomerate, (c) dissolved in a suitable non-polar good solvent first to form a metal-supported micelle and subsequently agglomerated using a suitable non-polar poor solvent, or (d) dissolved in a polar good solvent first to which a suitable non-polar solvent is subsequently added to form a metal-supported micelle and agglomerated using a non-polar poor solvent. In this case, the hydrophobic side chains are positioned inward in the micelle formed and the hydrophilic side chains are positioned outward in the micelle in methods (a) and (b), and the hydrophobic side chains are positioned outward in the micelle formed and the hydrophilic side chains are positioned inward in the micelle in methods (c) and (d).

The metal clusters are supported by the interaction with the hydrophobic side chains in individual micelles. In layered micelles and composite micelles, the positions of the hydrophobic and hydrophilic side chains are decided accordingly. The micelles prepared in the manner described are also present in a polymer-supported metal cluster composition of the present invention.

Now tetrahydrofuran (THF), dioxane, acetone, N,N-dimethyl formamide (DMF), N-methyl-2-pyrrolidone (NMP) and the like may be used as polar good solvents, and toluene, cyclohexane, dichloromethane, chloroform and the like may be used as non-polar good solvents. Methanol, ethanol, butanol, amyl alcohol and the like may be used as polar poor solvents, and hexane, heptane, octane and the like may be used as non-polar poor solvents. The concentration of a metal-containing polymer micelle varies according to the solvent, but the micelles are agglomerated while maintaining spherical shapes to eventually yield spherical or almost spherical cross-linked metal-containing polymer micelles when the concentration in a polar solvent is as low as from about 0.1 mg/ml to 100 mg/ml or particularly from about 0.1 mg/ml to 10 mg/ml. In addition, a morphological change occurs in the micelles when the concentration in a polar solvent is as high as from about 10 mg/ml to 100 mg/ml, and the micelles change to rod shaped micelles through lamellar micelles resulting in a three-dimensionally connected network structure of a spherical or rod shaped micelles.

Here, a metal precursor means a suitable compound (for example, an oxide, halide, a complex with ligands and the like) containing a desired transition metal, but a metal chelate (complex) formed with suitable ligands is preferred. When such a ligand complex is used, the metal in the precursor is supported on a polymer through a ligand exchange with hydrophobic groups (for example, aromatic groups and the like) present in a polymer with the structure described above. Now the valence of the supported metal can be reduced to zero by conducting a reduction treatment at the time a micelle is formed if the valence on the metal in the metal precursor is not zero.

As the ligand used to form a complex, organo phosphine ligands such as dimethylphenyl phosphine $[P(CH_3)_2Ph]$, diphenyl phosphino ferrocene ((dPPf), trimethyl phosphine $[P(CH_3)_3]$, triethyl phosphine $[P(Et)_3]$, tri-tert-butyl phosphine $[P(Bu)_3]$, tricyclohexyl phosphine $(Pcy_3)$, trimethoxy phospine $(P(OCH_3)_3)$, triethoxy phosphine $[P(OEt)_3]$, tri-tert-butoxy phosphine $[P(O^tBu)_3]$, triphenyl phosphine $(PPh_3)$, 1,2-bis(diphenyl phosphino) ethane (DPPE), triphenoxy phosphine $[P(OPh)_3]$, tri-o-tolyl phosphine, tri-m-tolyl phosphine, tri-p-tolyl phosphine and the like, 1,5-cyclooctadiene (COD), dibenzylidene acetone (DBA), bipyridine (BPY), phenanthroline (PHE), benzonitrile (PhCN), isocyanides (RNC), triethylarsine $[As(Et)_3]$, a halogen atom such as the fluorine atom, the chlorine atom, the bromine atom, the iodine atom and the like, acetyl acetonate, cyclooctadiene, cyclopentadiene, pentamethyl cyclopentadiene, ethylene, carbonyls, acetates, trifluoroacetates, biphenyl phosphine, ethylene diamine, 1,2-diphenyl ethylene diamine, 1,2-diamino cyclohexane, acetonitrile, hexafluoroacetylacetonate, sulfonates, carbonates, hydroxides, nitrates, perchlorates, sulfates and the like, for example, may be cited. Of these, organo phosphine ligands, 1,5-cyclooocatadiene (COD), dibenzylidene acetone (DBA), bipyridine (BPY), phenanthroline (PHE), benzonitrile (PhCN), isocyanides (RNC) and triethylarsine $[As(Et)_3]$ are preferred, triphenyl phosphine, tri-tert-butyl phosphine, and tri-o-tolyl phosphine are more preferred and triphenyl phosphine is particularly preferred.

The number of ligands is affected by the type of polymer used, the type of metal, the cross-linking reaction and the like used during the preparation, but one to six ligands are ordinarily used.

A polymer of the present invention needs to have a hydrophobic side chain (an aromatic group and the like) and a cross-linkable hydrophilic side chain (an amphiphilic polymer). That is, these side chains are directly bonded to a main polymer chain. The polymer may also contain multiple types of side chains.

As the hydrophobic side chain, aromatic groups, alkyl groups and the like may be cited.

The presence of aromatic groups is preferred.

As the aromatic groups, aryl groups and aralkyl groups may be cited.

As the aryl groups, those containing six to ten carbon atoms are ordinarily cited and those containing six carbon atoms are preferred. More specifically, phenyl groups, naphthyl groups and the like, for example, may be cited.

Now the number of carbon atoms defined in the present specification does not include the number of carbon atoms in the substituents on the group.

As the aralkyl groups, those containing seven to twelve carbon atoms are ordinarily cited and those containing seven to ten are preferred. More specifically, benzyl groups, phenylethyl groups, phenylpropyl groups, phenylbutyl groups, phenylpentyl groups, phenylhexyl groups and the like, for example, may be cited.

The aromatic ring in aryl and aralkyl groups may contain hydrophobic substituents such as alkyl groups, aryl groups, aralkyl groups and the like. The presence of hydrophilic substituents and reactive groups is undesirable.

As the alkyl groups that may be present in an aromatic ring, linear, branched or cyclic alkyl groups are acceptable. If cyclic alkyl groups are present, the groups may be monocyclic or polycyclic. Alkyl groups containing one to twenty carbon atoms are ordinarily used, but those containing one to twelve carbon atoms are preferred. More specifically, a methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, n-heptyl group, isoheptyl group, sec-heptyl group, tert-heptyl group, n-octyl group, sec-octyl group, tert-octyl group, nonyl group, decyl group, undecyl group, dodecyl group, tridecyl group, tetradecyl group, pentadecyl group, hexadecyl group, heptadecyl group, octadecyl group, nonadecyl group, icosyl group, cyclopropyl group, cyclopentyl group, cyclohexyl group, cycloheptyl group, cyclooctyl group, cyclononyl group, cyclodecyl group, cycloundecyl group, cyclododecyl group, cyclotridecyl group, cyclohexadecyl group, cyclooctadecyl group, cycloicosyl group and the like, for example, may be cited.

As the aryl and aralky groups that may be present in an aromatic ring, the same aryl and aralkyl groups listed above as aromatic groups may be cited.

The substituents that may be present in an aromatic ring may ordinarily substitute from one to five positions on the aromatic ring in the aryl and aralkyl groups, but one to two substitutions are preferred.

As the alkyl group in a hydrophobic side chain, the same alkyl groups that may be present in the aromatic ring as described above may be cited.

The hydrophilic side chains containing cross-linkable functional groups may comprise only hydrophilic cross-linkable functional groups or main chains of hydrophilic side chains containing cross-linkable functional groups. However, main chains of hydrophilic side chains containing cross-linkable functional groups are preferred.

As the cross-linkable functional group, an epoxy group, a carboxyl group, an isocyanate group, an isothiocyanate group, a hydroxyl group, a primary or secondary amino group and a thiol group may be cited. However, an epoxy group, a carboxyl group and an isocyanate group are preferred cross-linkable functional groups, an epoxy group and a carboxyl group are more preferred and an epoxy group is the most preferred group. These groups may be protected with suitable groups.

In addition, the polymer may also contain hydroxyl groups, primary or secondary amino groups and thiol groups when the cross-linkable function group is an epoxy group, a carboxyl group, an isocyanate group or an isothiocyanate group.

In this case, the hydroxyl group or primary or secondary amino group is preferred, and the hydroxyl group is more preferred.

As the preferred combinations for the cross-linkable functional groups present in a polymer, epoxy groups alone, epoxy and hydroxyl groups, epoxy and amino groups, epoxy and carboxyl groups, isocyanate or isothiocyanate group alone, isocyanate and hydroxyl groups, isocyanate and amino groups, isocyanate and carboxyl groups, carboxyl groups alone, hydroxyl groups alone, hydroxyl and carboxyl groups, carboxyl and amino groups and the like may be cited. Of these, epoxy groups alone and a combination of epoxy and hydroxyl groups are preferred.

The cross-linkable functional groups may be present in the same hydrophilic side chains or different hydrophilic side chains when multiple types of cross-linkable functional groups are contained in a polymer, but the presence of such functional groups in different hydrophilic side chains is preferred.

The main chain of hydrophilic side chains may be relatively short alkylene groups, for example, alkylene groups with about one to six carbon atoms, but those with main chains represented by $—R^9(OR^{10})_m—$, $—R^9(COOR^{10})_n—$ or $R^9(COOR^{10})_o(OR^{10})_p—$ (in the formulae $R^9$ represents a covalent bond or an alkylene group with one to six carbon atoms, preferably a covalent bond or an alkylene group with one to two carbon atoms, $R^{10}$ is individually independently alkylene groups with two to four carbon atoms, preferably with two carbon atoms, m, n and p are integers of one to ten and o represents one or two) are preferred since they are hydrophilic. As such preferred main chains, $—CH_2(OC_2H_4)_4—$, $—CO(OC_2H_4)_4$ and the like may be cited.

The polymer may be any polymer as long as it has these side chains, but those obtained by allowing a monomer containing the side chain to polymerize are preferred.

As such a monomer, that containing a double or triple bond for addition polymerization, for example, a vinyl group, an acetylene group and the like may be used. However, that containing a vinyl group is preferred.

That is, a preferred cross-linkable polymer is (A) a polymer or a copolymer obtained by allowing to polymerize or copolymerize at least one type of 1) a monomer containing a hydrophobic side chain, a hydrophilic side chain containing a cross-linkable functional group and a polymerizable double bond or (B) a copolymer obtained by allowing to copolymerize at least two monomers selected from groups consisting of 1) a monomer containing a hydrophobic side chain, a hydrophilic side chain containing a cross-linkable functional group and a polymerizable double bond, 2) a monomer containing a hydrophobic side chain and a polymerizable double bond and 3) a monomer containing a hydrophilic side chain containing a cross-linkable functional group and a polymerizable double bond. Here, the same type of monomers may also contain at least two different monomers.

1) The monomer containing a hydrophobic side chain, a hydrophilic side chain containing cross-linkable functional group and a polymerizable double bond represented by the following chemical Formula 1:

is preferred.

$R^1$ represents a hydrogen atom or an alkyl group with one to six carbon atoms, and a hydrogen atom is preferred.

$R^2$ represents an aryl group with six to fourteen carbon atoms with six preferred, and a phenyl group, a naphthyl group and the like, for example, may be cited. A phenyl group is preferred.

$R^3$ is the same as the main chain described above and represents $-R^9(OR^{10})_m-$, $-R^9(COOR^{10})_n-$ or $R^9(COOR^{10})_o(OR^{10})_p-$ (in the formulae $R^9$ represents a covalent bond or an alkylene group with one to six carbon atoms, $R^{10}$ is individually independently an alkylene group with two to four carbon atoms, m, n and p are integers of one to ten and o represents one or two).

$R^4$ represents a carboxyl group, an isocyanate group, an isothiocyanate group, a hydroxyl group, a primary or secondary amino group, a thiol group or an epoxy group represented by the formulae below (Chemical formula 2 or 3). An epoxy group, a carboxyl group and an isocyanate group are preferred, an epoxy group and a carboxyl group are more preferred and an epoxy group is most preferred. They may also be protected with suitable groups.

Chemical Formula 2:

Chemical Formula 3:

In the formulae, $R^5$ represents an alkylene group with one to six carbon atoms, preferably one to four and more preferably one to two. This alkylene group may be linear, branched or cyclic, and, for example, a methylene group, an ethylene group, a trimethylene group, a propylene group, a methyl methylene group, a methyl ethylene group, an ethyl methylene group, a tetramethylene group, a pentamethylene group, a hexamethylene group, a cyclopropylene group, a cyclopentylene group, a cyclohexylene group and the like may be cited.

$R^6$ and $R^7$ each independently represent a hydrogen atom or an alkyl group with one to six carbon atoms, preferably one to four, more preferably one to two, and a hydrogen atom is preferred.

$R^6$ may form a three to six membered carbon ring bonded with $R^5$ or $R^7$. As the three to six membered ring, a cyclopropane ring, a cyclobutane ring, a cyclopentane ring, a cyclohexane ring and the like, for example, may be cited.

2) The monomer containing a hydrophobic side chain and a polymerizable double bond represented by the following chemical formula 4:

is preferred.

$R^1$ and $R^2$ are independently defined as described above.

$R^{11}$ represents a hydrogen atom or an alkyl group with one to six carbon atoms, preferably one to four and more preferably one to two.

As this type of monomer, styrene type monomers are preferred. As the styrene type monomer, styrene, α-methylstyrene, β-methylstyrene, α-ethylstyrene, o-methylstyrene, m-methylstyrene, p-methylstyrene and the like may be cited. Of these, styrene and α-methylstyrene are preferred, and styrene is particularly preferred.

3) The monomer containing a hydrophilic side chain containing a cross-linkable functional group and a polymerizable double bond represented by the following Chemical Formula 5:

is preferred.

In the formula, $R^1$, $R^3$, $R^4$ and $R^{11}$ are independently defined as described above.

As such a polymer, for example, those containing two units selected from units (monomers) 1-3 shown below, those containing all units 1-3 and the like may be cited.

In the formulae, m represents an integer in which two of m are the same or different, X and X' represent, for example, epoxy groups and hydrogen atoms individually. In addition, x, y and z represent zero or positive integers. Unit 1 contains only hydrophobic side chains (aromatic groups), unit 2 contains both hydrophobic side chains (aromatic groups) and hydrophilic side chains and unit 3 contains only hydrophilic side chains. An important issue here is to strike a balance between the hydrophobic and hydrophilic side chains by combining these units. A combination of from 30 mole % to 100 mole % of the units containing hydrophobic side chains (in this example, unit 1+unit 2) and from 0.5 mole % to 100 mole % of the units containing hydrophilic side chains (in this example, unit 2+unit 3) is preferred.

Now a portion of the aromatic groups in unit 1 and/or unit 2 may be replaced with other hydrophobic side chains (alkyl groups).

The vinyl monomer corresponding to units 2 and 3 can be obtained subsequent to an etherification reaction of the vinyl halide compound described below with, for example, poly (ethylene glycol) and furthermore by an etherification reaction of, for example, a halogenated epoxy compound such as epichlorohydrin.

In the formula, X" represents a halogen atom and R represents a hydrogen atom or an alkyl group.

A micelle can be formed by dissolving such a polymer and a metal precursor described above in a suitable solvent described above and further adding other solvents as needed.

The metal precursor is first incorporated in the hydrophobic segment of the micelle in this case, and a metal cluster is formed by releasing the ligands coordinated in the metal precursor or by a reduction treatment. The metal cluster is also stabilized in a micro state upon receiving electron donation from the aromatic ring of the polymer.

The micelle size is ordinarily 5 nm to 3 μm with from 10 nm to 1 μm preferred and from about 10 nm to 500 nm more preferred.

The average diameter of one metal cluster supported thus is 20 or smaller with from 0.3 nm to 20 nm preferred, from 0.3 nm to 10 nm more preferred, from 0.3 nm to 5 nm even more preferred, from 0.3 nm to 2 nm even further more preferred and from 0.3 nm to 1 nm even further more and more preferred. The thinking is that numerous metal clusters are uniformly dispersed in the hydrophobic segment of the micelle. An excellent catalytic activity can be displayed (see Example 2 described later) since the metal is in the form of micro clusters (micro metal masses) in the manner described.

The metal cluster diameter can be measured using a transmission type electron microscope (TEM) or an extended X ray absorption fine structure spectrum (EXAFS).

A TEM allows only the metal section to be observed without a dye treatment. The cluster size is indicated to be smaller than 1 nm when the cluster is not observed with a TEM observation since the limit in the degree of resolution is about 1 nm.

An EXAFS spectrum is an interference spectrum of the photoelectrons discharged from an atom by X ray irradiation and the backscattering of the photoelectrons reflected by neighboring atoms, and appears on the higher energy side of the absorption edge in an X ray absorption spectrum. The information on the type of neighboring atoms, the interatomic distance and number of atoms (coordination number: CN) are obtained by analyzing this EXAFS spectrum. The coordination number particularly allows the number of assembled atoms and cluster diameters to be estimated. For example, the coordination number and the cluster diameter for a palladium cluster consisting of 13 atoms, considered as stable cluster in the field of quantum chemistry, are 5.53 and 0.83 nm, respectively.

Micelle supporting metal clusters of the type described can be cross-linked using cross-linkable functional groups. The micelle is stabilized by cross-linking, and leaching of the supported metal cluster can be prevented.

A cross-linking reaction can link the cross-linkable functional groups amongst themselves in a polymer constituting a single micelle or link the adjacent micelles among themselves. Furthermore, these micelles can be linked to a suitable carrier by utilizing a cross-linking reaction.

A cross-linking reaction can be induced by heat and ultraviolet irradiation depending on the type of the cross-linkable functional groups. The cross-linking reaction may be conducted according to conventional well-known methods used to cross-link a linear organic polymer compound in addition to the methods mentioned above. For example, a method in which a cross-linking agent is used, a method in which a condensation agent is used, a method in which a radical polymerization catalyst such as a peroxide, an azo compound and the like are used, a method in which an acid or a base is added and heated, a method in which a combination of a dehydration condensation agent such as, for example, a carbodiimide and a suitable cross-linking agent is added, and the like may be used.

The temperature when cross-linking cross-linkable functional groups by heating is ordinarily from 50° C. to 200° C., but 70° C. to 180° C. is preferred and from 100° C. to 160° C. is more preferred.

The reaction time when allowing a heated cross-linking reaction to occur is ordinarily from 0.1 to one hundred hours, but from an hour to fifty hours is preferred and from two hours to ten hours more preferred.

When allowing a cross-linking reaction to occur using a cross-linking agent, polyamine compounds such as hexamethylene diamine, hexamethylene tetramine and the like, for example, polyols such as ethylene glycol, propylene glycol, glycerin and the like, for example, and polycarboxylic acids and their anhydrides such as malonic acid, succinic acid, glutaric acid, adipic acid, pimelic acid, maleic acid, fumaric acid and the like, for example, may be used as the cross-linking agent when the cross-linkable functional group is an epoxy group. Similarly, polyhydroxy compounds such as ethylene glycol, glycerin and the like, for example, and alkylene oxide compounds such as ethylene oxide, propylene oxide and the like, for example, may be used as the cross-linking agent when the cross-linkable functional group in a polymer is a carboxyl group. Similarly, polycarboxylic acids and their anhydrides such as malonic acid, succinic acid, glutaric acid, adipic acid, pimelic acid, maleic acid, fumaric acid and the like, for example, alkylene oxide compounds such as ethylene oxide, propylene oxide and the like, for example, and polyamine compounds such as hexamethylene diamine, hexamethylene tetramine and the like, for example, may be used as the cross-linking agent when the cross-linkable functional group in a polymer is a hydroxyl group. Similarly, water, for example, polyhydroxy compounds such as ethylene glycol, glycerin and the like, for example, polycarboxylic acids and their anhydrides such as malonic acid, succinic acid, glutaric acid, adipic acid, pimelic acid, maleic acid, fumaric acid and the like, for example, and polyamine compounds such as hexamethylene diamine, hexamethylene tetramine and the like, for example, may be used as the cross-linking agent for a polymer containing monomer units derived from a monomer containing isocyanate groups as the cross-linkable functional group. Similarly, polycarboxylic acids and their anhydrides such as malonic acid, succinic acid, glutaric acid, adipic acid, pimelic acid, maleic acid, fumaric acid and the like, for example, and alkylene oxide compounds such as ethylene oxide, propylene oxide and the like, for example, may be used as the cross-linking agent when the cross-linkable functional group in a polymer is an amino group. As the condensation agent used to conduct cross-linking using a condensation agent, dehydration agents such as carbodiimides, for example, dicyclohexyl carbodiimide and the like, may be cited as the cross-linkable functional groups.

The amount of a cross-linking agent added is influenced by the reactivity of the cross-linking reaction, the molecular weight of the polymer, the reaction conditions and the like, but the amount added ordinarily delivers from 0.1 equivalent to ten equivalents, preferably from 0.5 equivalent to two equivalents and more preferably from 0.8 equivalent to 1.2 equivalents of the reactive functional groups (twice for difunctional cross-linking agents) of a cross-linking agent per cross-linkable functional group. The amount may be appropriately increased or decreased according to the properties (for example, flexibility, swelling properties and the like) desired from the target cross-linked type polymer composition.

The amount of a condensation agent is influenced by the reactivity of the cross-linking reaction, the molecular weight of the polymer, reaction conditions and the like, but the amount added ordinarily delivers from 0.1 equivalent to twenty equivalents, preferably from 0.5 equivalent to ten equivalents and more preferably from one equivalent to three equivalents of the condensation agent per cross-linkable functional group. The amount may be appropriately increased or decreased according to the properties (for example, flexibility, swelling properties and the like) desired from the target cross-linked type polymer composition.

The micelle may be used preferably in the form of a mass or a film containing a three-dimensional network structure or immobilized on a carrier. The polymer-supported metal cluster composition of the present invention is firmly immobilized on a carrier surface when the cross-linkable functional groups (for example, hydroxyl groups, amino groups and the like) on the surface of a carrier such as glass, silica gel, resin and the like and the cross-linkable functional groups on metal-containing polymer micelles are allowed to undergo a cross-linking reaction. In addition, a catalyst-supported reaction vessel that is simple to reuse can be obtained when a polymer-supported metal cluster composition of the present invention is immobilized on the surface of a reaction vessel made with a suitable resin or glass using the cross-linkable functional groups of a micelle.

A polymer micelle obtained in the manner described containing a cross-linked metal contains many cavities, and the supported metal forms very small clusters measuring less than several nano meters. Therefore, the polymer micelle obtained exhibits excellent activity in various reactions. This cross-linked polymer micelle can be used in hydrogenation reactions, oxidation reactions, dehydrogenation reactions, allylic substitution reactions, coupling reactions and the like. A particularly high activity is displayed when palladium is used as the metal.

The present invention is illustrated below using examples, but the intent of the examples is not to restrict the present invention.

PRODUCTION EXAMPLE 1

A mixture of 2-phenylpropene (22.4 g, 190 mmoles), N-bromosuccinimide (23.7 g, 133 mmoles) and bromobenzene (76 ml) was superheated on an oil bath at 160° C. until the N-bromosuccinimide was dissolved. The reaction mixture was cooled to room temperature, and the precipitate was subsequently removed by filtration and washed with chloroform. The filtrate was purified by distillation under reduced pressure to obtain 12.1 g of 3-bromo-2-phenylpropene (b.p. 80° C. to 85° C./3 mmHg). $^1$H-NMR (CDCl$_3$)δ=4.39 (s, 2H), 5.49 (s, 1H), 5.56 (s, 1H), 7.33-7.51 (m, 5H); $^{13}$C NMR (CDCl$_3$)δ=34.2, 117.2, 126.1, 128.3, 128.5, 137.6, 144.2.

Five milliliters of a DMF solution of glycidol (7.4 g, 100 mmoles) was added to a suspension of 60% sodium hydride (1.6 g, 40 mmoles) (75 ml) at 0° C. Next, a DMF (10 ml) solution of the 3-bromo-2-phenylpropene (3.94 g, 20 mmoles) obtained as described above was added at the same temperature, and the mixture was subsequently agitated for 24 hours at room temperature. The reaction mixture was cooled to 0° C. and subsequently diluted with diethyl ether, and the reaction was terminated by adding a saturated aqueous ammonium chloride solution. The aqueous layer was extracted several times with diethyl ether, and the organic layers were combined and dried using anhydrous sodium sulfate. The solvent was concentrated after filtration, and the residue was purified using silica gel chromatography (Hexane-AcOEt) to obtain 2-[(2-phenyl allyloxy)methyl] oxylane (2.66 g, 70%). $^1$H NMR (CDCl$_3$) δ=2.59 (dd, 1H, J=2.7 Hz, 5.1 Hz), 2.78 (dd, 1H, J=4.2 Hz, 5.1 Hz), 3.13-3.17 (m, 1H), 3.46 (dd, 1H, J=5.8, 11.5 Hz), 3.77 (dd, 1H, J=3.2, 11.5 Hz), 4.41 (ddd, 1H, J=0.7, 1.2, 12.9 Hz), 4.48 (ddd, 1H, J=0.5, 1.2, 12.9 Hz), 5.34-5.36 (m, 1H), 5.53-5.54 (m, 1H), 7.45-7.48 (m, 5H); $^{13}$C NMR (CDCl$_3$)δ=44.3, 50.8, 70.5, 73.2, 114.6, 126.0, 127.8, 128.4, 138.6, 143.9; IR (KBr) 3000, 2924, 2867, 1911, 1812, 1701, 1630, 1512, 1479, 1407, 1337, 1254, 1205, 1107, 991, 909, 839 cm$^{-1}$; HRMS (EI): Calculated for $C_{13}H_{16}O_2(M^+)$ 190.0994, found 190.0998.

Styrene (12.5 g, 120 mmoles), the 2-[(2-phenyl allyloxy) methyl] oxylane (2.85 g, 15 mmoles) obtained as described above, tetraethyleneglycol mono-2-phenyl-2propenyl ether (4.66 g, 15 mmoles) and AIBN (174.2 mg, 1.05 mmoles) were dissolved in chloroform (19 ml), heated and agitated in an argon atmosphere under reflux conditions for 48 hours. The reaction mixture after cooling was poured into methanol (MeOH, 600 ml) to solidify the polymer. The product obtained was decanted to remove the supernatant solution, and the solids were subsequently dissolved in a small amount of tetrahydrofuran and again poured into methanol. The precipitated polymer was filtered and dried at room temperature under reduced pressure to obtain 12.0 g of a polymer (60% yield).

The polymer obtained had the structure shown below, and the composition ratio (x/y/z) of the individual monomer units was 91/5/4. The weight average molecular weight (Mw) was 31,912, the number average molecular weight (Mn) was 19,468 and the degree of dispersion (Mw/Mn) was 1.64. The polymer formed is henceforth referred to as Polymer (1).

EXAMPLE 1

Synthesis of a Polymer-Supported Pd Cluster Composition

Polymer (1) (2.0 g) and Pd(PPh$_3$)$_4$ (2.0 g) were dissolved in 40 ml of dichloromethane (DCM) and were agitated for twelve hours. Forty milliliters of methanol was gradually added to this solution to form micelles, and 80 ml of methanol was subsequently added to agglomerate the micelles. The supernatant solution was removed by decantation, and the solids were washed several times with methanol before drying them under reduced pressure. The solids were subsequently heated for two hours at 120° C. to cross-link the micelles. The micelles were washed with THF and subsequently dried to obtain 1.9 g of a polymer-supported Pd cluster composition. The Pd concentration was 0.40 mmoles/g.

Figure 1:
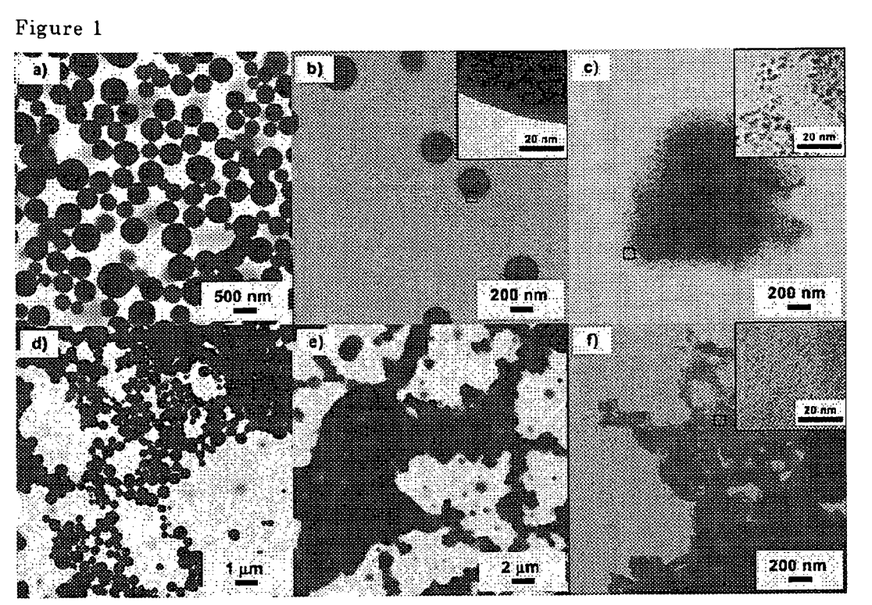
FIG. 1 is a transmission electron microscope (TEM) photograph of a polymer-supported metal cluster composition of the present invention. (a) shows a polymer-Pd micelle in a DCM-$^t$AmOH=1/5 solution, (b) shows the micelle after cross-linking by heating, (c) shows a polymer-Pd micelle after cross-linking by microwave irradiations, (d) shows a polymer-Pd micelle in a DCM-MeOH=1/1 solution, (e) shows a polymer-Pd micelle in a DCM-MeOH=1/2 solution and (f) shows a cross-linked polymer-Pd micelle in a DCM-MeOH=1/3 solution.
Figure 2:
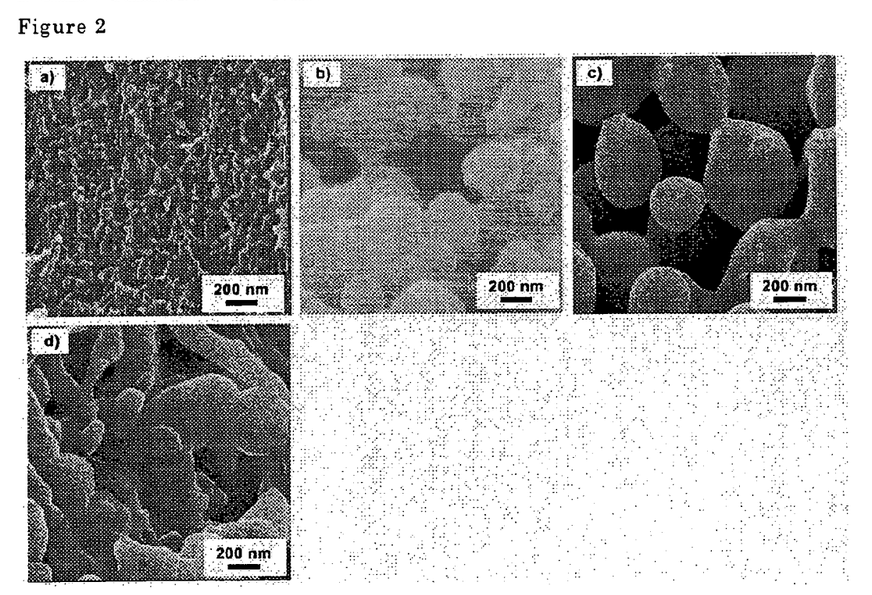
FIG. 2 is a scanning electron microscope (SEM) photograph of a polymer-supported metal cluster composition of the present invention. (a) shows the three dimensional network structure of a polymer-Pd micelle, (b) shows a micelle immobilized on glass, (c) shows a micelle immobilized on a hydroxymethylated resin and (d) shows a micelle immobilized on an aminomethylated resin.

When the micelles were allowed to agglomerate at a high concentration, the micelles underwent a morphology change from spherical micelles (FIG. 1d) through lamellar micelles (FIG. 1e) to rod shaped micelles. Further, by cross-linking the micelles, polymer micelles (FIGS. 1f and 2a) containing a cross-linked metal having a three dimensional network structure are obtained. The micelles were shaped in the form of three dimensional network structures containing cavities comprising spherical or rod shape micelles (FIGS. 1f and 2a). The diameters of the spherical to rod shaped micelles were from about 20 to 50 nm, and the relative surface areas (determined using a BET method) were 50.92 m$^2$/g.

The palladium cluster was not observed in a TEM measurement indicating that the cluster size was less than one nm (FIG. 1f). In addition, an X ray absorption spectrum of the composition obtained was measured using a 10B beam line in a High Energy Physics Laboratory (KEK) radiation photon experimental facility (Photon Factory, PF), and an EXAFS analysis was conducted. The results indicated that the Pd—Pd inter-atomic distance, r, was equal to 2.76 Å, and the coordination number (CN) was 4.4. The results indicated that Pd was in zero valence and in the form of clusters containing an average of seven Pd atoms. The diameter of the cluster was estimated to be about 0.7 nm.

EXAMPLE 2

Synthesis of a Polymer-Supported Pd Cluster Composition

Polymer (1) (500 mg) and Pd(PPh$_3$)$_4$ (500 mg, 0.43 mmoles) were dissolved in 10 ml of dichloromethane and added gradually to 50 ml of t-amyl alcohol (t-AmOH) to form micelles (FIG. 1a). The reaction system was subsequently agitated for eight hours. The reaction vessel was sealed, and the micelles were cross-linked by heating and agitating the reaction mixture for five hours at 120° C. The micelles formed were poured into methanol to solidify, and the precipitate was subsequently filtered and was dried at room temperature under reduced pressure to yield 534 mg of cross-linked polymer micelles containing Pd. The Pd concentration was 0.81 mmoles/g. The micelles were spherical, and their diameters were from about 200 nm to 500 nm (FIG. 1b). Palladium clusters were not observed in a TEM measurement indicating that the cluster diameter was less than one nm.

The metal-containing polymer micelles dispersed in a micelle solution could be cross-linked while maintaining their spherical shapes (FIG. 1b) when the micelles were agglomerated at a low concentration, but agglomeration on a carrier as described above was desirable when the metal-containing polymer micelles were isolated using filtration and the like.

EXAMPLE 3

Synthesis of a Polymer-Supported Pd Cluster Composition Supported on a Silica Gel Polymer (1) (200 mg) and Pd(PPh$_3$)$_4$ (200 mg, 0.17 mmoles) were dissolved in 20 ml of dichloromethane, and 100 ml of t-amyl alcohol was gradually added to form micelles. Silica gel (2.0 g) was added to the micelles formed to agglomerate the micelles on the silica gel. The supernatant solution was removed by decantation, and the solids were washed several times with methanol before drying under reduced pressure. The solids were subsequently heated for two hours at 120° C. to cross-link the micelles. A polymer-supported Pd cluster composition (2.05 g) supported on silica gel was obtained after the solids were washed using THF and dried. The Pd concentration was 0.043 mmole/g. The micelles were spherical, and their diameters were from about 200 nm to 500 nm.

EXAMPLE 4

Synthesis of a Polymer-Supported Pd Cluster Composition Supported on Aminopropylated Silica Gel Polymer (1) (200 mg) and Pd(PPh$_3$)$_4$ (200 mg, 0.17 mmoles) were dissolved in 20 ml of dichloromethane, and 100 ml of t-amyl alcohol was gradually added to form micelles.

Aminopropylated silica gel (Fuji Silicia K.K., trade name FM1020) (2.0 g) was added to the micelles formed to agglomerate the micelles on the aminopropylated silica gel. The supernatant solution was removed by decantation, and the solids were washed several times using methanol before drying under reduced pressure. The solids were subsequently heated for two hours at 120° C. to cross-link the micelles. A polymer-supported Pd cluster composition (1.89 g) supported on silica gel was obtained after the solids were washed with THF and dried. The Pd concentration was 0.043 mmole/g.

The micelles were spherical or rod shaped, and their diameters were from about 100 nm to 500 nm.

EXAMPLE 5

Synthesis of a Polymer-Supported Pd Cluster Composition Supported on a Hydroxymethylated Resin Polymer (1) (200 mg) and Pd(PPh$_3$)$_4$ (200 mg, 0.17 mmoles) were dissolved in 20 ml of dichloromethane, and 100 ml of t-amyl alcohol was gradually added to form micelles. A hydroxymethylated resin (Nova Biochem Co., trade name Hydroxymethylpolystyrene, from 100 mesh to 200 mesh) (2 g) was added to the micelles formed to agglomerate the micelles on the hydroxymethylated resin. The supernatant solution was removed by decantation, and the solids were washed several times using methanol before drying under reduced pressure. The solids were subsequently heated for two hours at 120° C. to cross-link the micelles. A polymer-supported Pd cluster composition (1.73 g) supported on hydroxymethylated resin was obtained after the solids were washed with THF and dried. The Pd concentration was 0.009 mmole/g. The micelles were spherical, and their diameters were from about 200 nm to 500 nm (FIG. 2c).

EXAMPLE 6

Synthesis of a Cross-linked Pd Cluster Composition Supported on a Hydroxymethylated Resin Polymer (1) (200 mg) and Pd(PPh$_3$)$_4$ (200 mg, 0.17 mmoles) were dissolved in 20 ml of dichloromethane, and 100 ml of t-amyl alcohol was gradually added to form micelles. The same hydroxymethylated resin (10 g) used in Example 5 was added to the micelles formed to agglomerate the micelles on the hydroxymethylated resin. The supernatant solution was removed by decantation, and the solids were washed several times with methanol before drying under reduced pressure. The solids were subsequently heated for two hours at 120° C. to cross-link the micelles. A cross-linked Pd cluster composition (9.80 g) supported on a hydroxymethylated resin was obtained after the solids were washed with THF and dried. The Pd concentration was 0.00078 mmole/g. The cross-linked Pd cluster composition of the present example had a lower palladium concentration than the cross-linked Pd cluster composition of Example 5.

EXAMPLE 7

Synthesis of a Polymer-Supported Pd Cluster Composition Supported on an Aminomethylated Resin Polymer (1) (200 mg) and $Pd(PPh_3)_4$ (200 mg, 0.17 mmoles) were dissolved in 20 ml of dichloromethane, and 100 ml of t-amyl alcohol was gradually added to form micelles. An aminomethylated resin (Nova Biochem Co., trade name Aminomethylated Polystyrene HL, from 100 mesh to 200 mesh) (2 g) was added to the micelles formed to agglomerate the micelles on the hydroxymethylated resin. The supernatant solution was removed by decantation, and the solids were washed several times with methanol before drying under reduced pressure. The solids were subsequently heated for two hours at 120° C. to cross-link the micelles. A polymer-supported Pd cluster composition (1.52 g) supported on an aminomethylated resin was obtained after the solids were washed with THF and dried. The Pd concentration was 0.0037 mmole/g. The micelles were spherical or rod shaped, and their diameters were from about 100 nm to 500 nm (FIG. 2d).

EXAMPLE 8

Synthesis of a Polymer-Supported Pd Cluster Composition Supported on Glass

Polymer (1) (200 mg) and $Pd(PPh_3)_4$ (200 mg, 0.17 mmoles) were dissolved in 20 ml of dichloromethane, and 100 ml of t-amyl alcohol was gradually added to form micelles. A microscope slide glass (one piece) was added to the micelles formed to agglomerate the micelles on the glass. The supernatant solution was removed by decantation, and the glass was washed several times with methanol before drying under reduced pressure. The glass was subsequently heated for two hours at 120° C. to cross-link the micelles. A polymer-supported Pd cluster composition supported on glass was obtained after the glass was washed with THF and dried. The Pd concentration was 0.002 mmole/g. The micelles were spherical, and their diameters were from about 200 nm to 500 nm (FIG. 2b).

EXAMPLE 9

Synthesis of a Cross-linked Ni Cluster Composition

Polymer (1) (500 mg) and $Ni(PPh_3)_4$ (443 mg) were dissolved in 10 ml of dichloromethane, and the solution was agitated for twelve hours. Methanol (10 ml) was gradually added to form micelles, and the micelles were agglomerated by subsequently adding an additional 20 ml of methanol. The supernatant solution was removed by decantation, and the solids were washed several times with methanol before drying under reduced pressure. The solids were subsequently heated for two hours at 120° C. to cross-link the micelles. A cross-linked Ni cluster composition (450 mg) was obtained after the solids were washed with THF and dried. The Ni concentration was 0.13 mmole/g.

EXAMPLE 10

Synthesis of a Cross-linked Ir Cluster Composition

Polymer (1) (500 mg) and $[IrCl(COD_2)]_2$ (67.2 mg) were dissolved in 10 ml of dichloromethane, and 50 ml of t-amyl alcohol was gradually added to form micelles. The micelles were agitated for sixteen hours at room temperature in one atmospheric pressure hydrogen atmosphere. Methanol (140 ml) was gradually added to agglomerate the micelles. The supernatant solution was removed by decantation, and the solids were washed several times with methanol before drying under reduced pressure. The solids were subsequently heated for two hours at 120° C. to cross-link the micelles. A cross-linked Ir cluster composition (288 mg) was obtained after the solids were washed with THF and dried. The Ir concentration was 0.69 mmole/g.

EXAMPLE 11

Synthesis of a Cross-linked Ir—Pt Cluster Composition

Polymer (1) (100 mg) and $[IrCl(COD_2)]_2$ (6.7 mg, 0.01 mmole) and $PtCl_2(COD)$ (3.71 mg, 0.01 mmole) were dissolved in 4 ml of dichloromethane, and 20 ml of t-amyl alcohol was gradually added to form micelles. The micelles formed were agitated for sixteen hours at room temperature in one atmospheric pressure hydrogen atmosphere. Methanol (130 ml) was added to the micelles to agglomerate them. The supernatant solution was removed by decantation, and the solids were washed several times with methanol before drying under reduced pressure. The solids were subsequently heated for two hours at 120° C. to cross-link the micelles. A cross-linked Ir—Pt cluster composition (23 mg) was obtained after the solids were washed with THF and dried. The Ir concentration was 0.87 mmole/g and the Pt concentration was 0.87 mmole/g.

EXAMPLE 12

Synthesis of a Cross-linked Ir—Au Cluster Composition

AuCl (11.62 mg, 0.05 mmole), (1,5-cyclooctadiene 21.6 mg, 0.1 mmole), the Polymer (1) (500 mg) and $[IrCl(COD_2)]_2$ (67.2 mg, 0.1 mmole) were dissolved in 10 ml of dichloromethane, and 50 ml of t-amyl alcohol was gradually added to form micelles. The micelles formed were agitated for sixteen hours at room temperature in a hydrogen atmosphere at one atmosphere pressure. Methanol (325 ml) was added to the micelles to agglomerate them. The supernatant solution was subsequently removed by decantation, and the solids were washed several times with methanol before drying under reduced pressure. The solids were subsequently heated for two hours at 120° C. to cross-link the micelles. A cross-linked Ir—Au cluster composition (248 mg) was obtained after the solids were washed with THF and dried. The Ir concentration was 0.61 mmole/g and the Au concentration was 0.20 mmole/g.

EXAMPLE 13

Synthesis of a Cross-linked Ir-Pt Cluster Composition

The cross-linked Ir cluster composition obtained in Example 10 (18.5 mg, 0.01 mmole) was mixed with dichloromethane (2 ml), and the mixture was agitated for thirty minutes at room temperature in a hydrogen atmosphere at one atmosphere pressure. To this solution was slowly added a dichloromethane (3 ml) solution of $PtCl_2(COD)$ (3.71 mg, 0.01 mmole), and the mixture was subsequently agitated for eight hours at room temperature. The mixture was filtered, the solids were washed several times with dichloromethane and were dried under reduced pressure to obtain 20 mg of a cross-linked Ir—Pt cluster composition. The Ir concentration was 0.61 mmole/g and the Pt concentration was 0.87 mmole/g.

EXAMPLE 14

Synthesis of a Cross-linked Pt-Containing Cluster Composition

Polymer (1) (500 mg) and $Pt(PPh_3)_4$ (500 mg) were dissolved in 10 ml of dichloromethane, and the solution was agitated for twelve hours. Methanol (10 ml) was gradually added to form micelles, and the micelles were agglomerated by subsequently adding an additional 20 ml of methanol. The supernatant solution was removed by decantation, and the solids were washed several times with methanol before drying under reduced pressure. The solids were subsequently heated for two hours at 120° C. to cross-link the micelles. A cross-linked Pt cluster composition (415 mg) was obtained after the solids were washed with THF and dried. The Pt concentration was 0.69 mmole/g.

EXAMPLE 15

Heck Reaction Using a Polymer-Supported Pd Cluster Composition

The polymer-supported Pd cluster composition obtained in Example 1 (labeled as PIPd in the equation above) (62.6 mg, 0.025 mmole), iodobenzene (102 mg, 0.5 mmole), ethyl acrylate (75.2 mg, 0.75 mmole), potassium carbonate (138.2 mg, 1 mmole) and N-methyl-2-pyrrolidinone (labeled as NMP in the equation above) (5 ml) were mixed and agitated for an hour at 120° C. The mixture was filtered after adding ethanol, and the polymer-supported Pd cluster composition was removed. The filtrate was concentrated, and the residue was extracted with diethyl ether. The organic layer was washed with saturated sodium chloride solution, dried using anhydrous sodium sulfate and subsequently concentrated. The residue was purified using preparative thin layer chromatography (PTLC) to obtain a purified ethyl cinnamate (81.9 mg, 93% yield). The polymer-supported Pd cluster composition was dried and used repeatedly in the same reaction. Ethyl cinnamate was obtained in 92% yield the second time, 91% yield the third time, 91% yield the fourth time and 92% yield the fifth time.

The target material was obtained in high yield using only an extremely small amount of the composition, and the composition was recovered and reused without any activity loss.

$^1$H NMR ($CDCl_3$) δ=1.34 (t, 3H, J=7.1 Hz), 4.27 (q, 2H, J=7.1 Hz), 6.44 (d, 1H, J=15.6 Hz), 7.36-7.39 (m, 3H), 7.51-7.53 (m, 2H), 7.69 (d, 1H, J=15.6 Hz); $^{13}$C NMR ($CDCl_3$) δ=14.3, 60.5, 118.3, 128.0, 128.9, 130.2, 134.5, 144.6, 167.0.

The Heck reaction conducted in the present example is shown in the equation below.

EXAMPLE 16

Heck Reaction Using a Polymer-Supported Pd Cluster Composition

The polymer-supported Pd cluster composition obtained in Example 1 (1.25 mg, 5×10$^{-4}$ mmole), iodobenzene (10.2 mg, 50 mmoles), ethyl acrylate (7.5 mg, 75 mmoles), potassium carbonate (13.8 g, 100 mmoles) and N-methyl-2-pyrrolidinone (50 ml) were mixed and agitated for twenty-four hours at 120° C. The mixture was filtered after adding ethanol, and the polymer-supported Pd cluster composition was removed. The filtrate was concentrated, and the residue was extracted with diethyl ether. The organic layer was washed with saturated sodium chloride solution, dried using anhydrous sodium sulfate and subsequently concentrated. The residue was purified using silica gel chromatography to obtain a purified ethyl cinnamate (7.3 g, 82.5% yield). The TON (turn over number) was 82,500.

EXAMPLE 17

Heck Reaction Using a Polymer-Supported Pd Cluster Composition Supported on a Hydroxymethylated Resin The polymer-supported Pd cluster composition supported on a hydroxymethylated resin obtained in Example 5 (55.6 mg, 5×10$^{-4}$ mmole), iodobenzene (10.2 mg, 50 mmoles), ethyl acrylate (7.5 mg, 75 mmoles), potassium carbonate (13.8 g, 100 mmoles) and N-methyl-2-pyrrolidinone (50 ml) were mixed and agitated for twenty-four hours at 120° C. The mixture was filtered after adding ethanol, and the polymer-supported Pd cluster composition was removed. The filtrate was concentrated, and the residue was extracted with diethyl ether. The organic layer was washed with saturated sodium chloride solution, dried using anhydrous sodium sulfate and subsequently concentrated. The residue was purified using silica gel chromatography to obtain a purified ethyl cinnamate (6.9 g, 78.2% yield). The TON (turn over number) was 78,200.

EXAMPLE 18

Heck Reaction Using a Cross-linked Pd Cluster Composition Supported on a Hydroxymethylated Resin The cross-linked Pd cluster composition supported on a hydroxymethylated resin obtained in Example 6 (19.1 mg, $1.5 \times 10^{-5}$ mmole), iodobenzene (1.02 mg, 5 mmoles), ethyl acrylate (0.75 mg, 7.5 mmoles), potassium carbonate (1.38 g, 10 mmoles) and N-methyl-2-pyrrolidinone (10 ml) were mixed and agitated for twenty-four hours at 120° C. The mixture was filtered after adding ethanol, and the cross-linked Pd cluster composition was removed. The filtrate was concentrated, and the residue was extracted with diethyl ether. The organic layer was washed with saturated sodium chloride solution, dried using anhydrous sodium sulfate and subsequently concentrated. The residue was purified using silica gel chromatography to obtain a purified ethyl cinnamate (0.82 g, 93% yield). The TON (turn over number) was 284,660.

EXAMPLE 19

Sonogashira Reaction Using a Cross-linked Pd Cluster Composition

The cross-linked Pd cluster composition obtained in Example 2 (12.5 mg, 0.005 mmole), 4'-iodoacetophenone (123.0 mg, 0.5 mmole), phenylactylene (63.8 mg, 0.625 mmole), cesium carbonate (325.8 mg, 1 mmole), N-methyl-2-pyrrolidinone (2 ml) and toluene (3 ml) were mixed and were agitated for eight hours at 80° C. The mixture was filtered after adding ethanol, and the cross-linked Pd cluster composition was removed. The filtrate was concentrated, and the residue was dissolved in acetonitrile (5 ml). The palladium concentration was subsequently measured using X ray fluorescence spectroscopy (XRF), and no palladium leaching was detected (the measurement limit value was 5 ppm). The solution was extracted by diethyl ether after the XRF measurement, and the organic layer was washed with saturated aqueous sodium chloride solution, dried using anhydrous sodium sulfate and concentrated. The reside was purified using PTLC, and 4-(phenylethenyl) acetophenone (85.9 mg, 78.0% yield) was obtained.

$^1$H NMR (CDCl$_3$) δ=$^1$H NMR (CDCl$_3$) δ=2.59 (s, 3H), 7.35-7.37 (m, 3H), 7.53-7.61 (m, 4H), 7.91-7.94 (m, 2H); $^{13}$C NMR (CDCl$_3$) δ=26.8, 88.9, 93.0, 122.9, 128.4, 128.5, 128.7, 129.1, 131.9, 132.0, 136.4, 197.5.

The Sonogashira reaction of the present example is shown by the equation below.

The supported Pd amount could be reduced by increasing the amount of the carrier (resin) used per Pd in comparison to Example 17. The process could take advantage of the catalyst diffusion and the reaction efficiency could be elevated in a reaction such as the one in the present example in which a very small amount of a catalyst was used.

EXAMPLE 20

Asymmetric Hydrogenation Reaction Using a Cross-linked Ir Cluster Composition The cross-linked Ir cluster composition obtained in Example 10 (14.4 mg, 0.01 mmole), methyl benzoyl formate (164.2 mg, 1.0 mmole), (−) cinchonidine (3.8 mg, 0.013 mmole) and toluene (5 ml) were mixed in an autoclave and agitated for five hours at room temperature in a hydrogen atmosphere at 50 atmospheres pressure. The cross linked Ir cluster composition was removed by filtration after the reaction. The filtrate was concentrated, and the residue was purified using PTLC to obtain (R)-methyl mandelate (147.1 mg, 88.5% yield). The asymmetric yield was 47.1% ee.

$^1$H NMR (CDCl$_3$) δ=$^1$H NMR (CDCl$_3$) δ=3.75 (s, 3H), 7.32-7.43 (m, 5H); $^{13}$C NMR (CDCl$_3$) δ=53.0, 72.8, 126.6, 128.5, 128.6, 138.2, 174.1.

The asymmetric hydrogenation of the present example was shown in the equation below.

EXAMPLE 21

Asymmetric Hydrogenation Reaction Using a Cross-linked Ir—Pt Cluster Composition The cross-linked Ir—Pt cluster composition obtained in Example 11 (10.0 mg), methyl benzoyl formate (164.2 mg, 1.0 mmole), (−) cinchonidine (3.8 mg, 0.013 mmole) and toluene (5 ml) were mixed in an autoclave and agitated for five hours at room temperature in a hydrogen atmosphere at a pressure of 50 atmospheres. The cross linked Ir—Pt cluster composition was removed by filtration after the reaction. The filtrate was concentrated, and the residue was purified using PTLC to obtain (R)-methyl mandelate (125 mg, 75% yield). The asymmetric yield was 52% ee.

EXAMPLE 22

Asymmetric Hydrogenation Reaction Using a Crosslinked Ir—Au Cluster Composition

The cross-linked Ir—Au cluster composition obtained in Example 12 (10.0 mg), methyl benzoyl formate (164.2 mg, 1.0 mmole), (−)cinchonidine (3.8 mg, 0.013 mmole) and toluene (5 ml) were mixed in an autoclave and agitated for hie hours at room temperature in a hydrogen atmosphere at a pressure of 50 atmospheres. The cross linked Ir—Au cluster composition was removed by filtration after the reaction. The filtrate was concentrated, and the residue was purified using PTLC to obtain (R)-methyl mandelate (160.5 mg, 96.5% yield). The asymmetric yield was 52.9% ee.

EXAMPLE 23

Asymmetric Hydrogenation Reaction Using a Cross-linked Ir—Pt Cluster Composition The cross-linked Ir—Pt cluster composition obtained in Example 13 (20.2 mg), methyl benzoyl formate (164.2 mg, 1.0 mmole), (−) cinchonidine (3.8 mg, 0.013 mmole) and toluene (5 ml) were mixed in an autoclave and agitated for five hours at room temperature in a hydrogen atmosphere at a pressure of 50 atmospheres. The cross linked Ir—Pt cluster composition was removed by filtration after the reaction. The filtrate was concentrated, and the residue was purified using PTLC to obtain (R)-methyl mandelate (165.6 mg, 99.7% yield). The asymmetric yield was 62.6% ee.

EXAMPLE 24

Preparation of a Polymer-Supported Metal Cluster Composition Film

Polymer micelles (50 mg) obtained in the manner described in Example 2 were mixed with 100 ml of a 2% aqueous gelatin solution to prepare a polymer dispersion composition. This dispersion composition was applied using a wire bar coater to a cellulose triacetate film previously coated with an aqueous gelatin solution and dried. The film was dried to obtain a film of a polymer-supported metal cluster composition on a cellulose triacetate film.

COMPARATIVE EXAMPLE 1

Styrene (13.42 mg, 128.9 mmoles), 4-vinylbenzyl glycidyl ether (3.06 g, 16.1 mmoles), tetraethylene glycol mono-2-phenyl-2-propenyl ether (5.0 g, 16.1 mmoles) and AIBN (189.6 mg, 1.15 mmoles) were dissolved in chloroform (20 ml) and heated and agitated in an argon atmosphere for forty-eight hours under reflux conditions. The reaction mixture was poured into methanol (600 ml) upon cooling to solidify the polymer. The supernatant solution was removed by decantation, and the solids were dissolved in a small amount of tetrahydrofuran and poured into methanol again. The polymer precipitated was filtered and dried at room temperature under reduced pressure to obtain 16.2 g of a polymer (76% yield). The structure of the polymer obtained is represented by the formula below. The polymer formed is henceforth referred to as Polymer (2).

The ratio in the polymer obtained for (styrene/4-vinyl benzylglycidyl ether/tetraethylene glycol mono-2-phenyl-2-propenyl ether) according to the $^1$H NMR measurement was the ratio of individual monomer units (x/y/z)=86/9/5. In addition, the weight average molecular weight (Mw) was 38,000.

Polymer (2) (2.0 g) and Pd(PPh$_3$)$_4$ (2.0 g) were dissolved in 40 ml of dichloromethane and were agitated for twelve hours. Methanol (120 ml) was gradually added to the solution to solidify the product. The supernatant solution was removed by decantation, washed several times with methanol and subsequently dried under reduced pressure.

The polymer was cross-linked by subsequently heating it for two hours at 120° C. The polymer was washed with THF first and dried to obtain a cross-linked Pd-containing polymer (2.0 g). The Pd concentration was 0.67 mmole/g.

The cross-linked Pd-containing polymer obtained (37.3 mg, 0.025 mmole), iodobenzene (102 mg, 0.5 mmole), ethyl acrylate (75.2 mg, 0.75 mmole), potassium carbonate (138.2 mg, 1 mmole) and N-methyl-2-pyrrolidinone (5 ml) were mixed and agitated for an hour at 120° C. The mixture was filtered after adding ethanol, and a polymer-supported Pd cluster composition was removed. The filtrate was concentrated, and the residue was dissolved in acetonitrile (5 ml). The palladium concentration was measured using an X ray fluorescence analytical device (XRF) and was 71.8 ppm. This corresponded to 13.5% of the amount of palladium in the composition used. The solution was extracted by diethyl ether after the XRF measurements were taken, the organic layer was washed with saturated sodium chloride solution, dried using anhydrous sodium sulfate and subsequently concentrated. The residue was purified using PTLC to obtain a purified ethyl cinnamate (70.8 mg, 80% yield).

The results from Example 15 and Comparative Example 1 and the results of measuring the amount of Pd leached into the solution are summarized in Table 1.

TABLE 1

| | Solvent system | Observed structure | Diameter of micelles (nm) | Yield of cinnamate (%) | Leaching of Pd (%) |
|---|---|---|---|---|---|
| Example 15 | MeOH-DCM | networked | 20-50 | 93 | nd |
| Comparative Example 1 | MeOH-DCM | networked | — | 80 | 13.5 |

In Example 15, no Pd leaching was observed (nd), but Pd leaching was observed in Comparative Example 1. The difference was attributed to the lack of micelle formation such as that observed in the polymer-supported metal cluster composition of the present invention in the cross-linked Pd-containing polymer used in Comparative Example 1. In addition, the yield was higher in Example 15 than in Comparative Example 1. The observation was thought to be related to a higher catalytic activity associated with the fine Pd clusters supported on the polymer-supported metal cluster composition.

COMPARATIVE EXAMPLE 2

Asymmetric Hydrogenation Reaction Using Iridium Carbon

Five percent Ir/C (38.4 mg, 0.01 mmole), methyl benzoyl formate (164.2 mg, 1.0 mmole), (−) cinchonidine (3.8 mg, 0.013 mmole) and toluene (5 ml) were mixed in an autoclave and were agitated for five hours at room temperature under hydrogen at a pressure of 50 atmospheres. The cross-linked Ir/C cluster composition was removed by filtration after the reaction. The filtrate was concentrated, and the residue was purified using PTLC to obtain (R)-methyl mandelate (145.4 mg, 87.5% yield). The asymmetric yield was 2.0% ee.

POTENTIAL INDUSTRIAL UTILITY

The present invention, as described above, provides a stable composition supporting extremely fine metal clusters by a polymer, that is, a polymer-supported metal cluster composition. Polymer-metal composite materials of a variety of shapes such as porous, spherical, rod-shaped, lamellar, film-shaped and the like can be prepared by using the composition. Such composite materials are thought to have potential applications not only as catalysts but also in various areas such as in materials used to manufacture a variety of functional films, fuel cell materials, chemical sensors, data storage devices, electrodes, selective adsorption filters, molecular sieve filters, adsorption agents, hydrogen storage agents and semiconductors.

What is claimed is:

1. A polymer-supported metal cluster composition comprising a transition metal and a cross-linked polymer, wherein the transition metal is supported by the cross-linked polymer and the cross-linked polymer is obtained by cross-linking a cross-linkable polymer wherein the cross-linkable polymer contains at least one hydrophobic side chain and at least one hydrophilic side chain, wherein at least one hydrophilic side chain has a cross-linkable functional group, and wherein each hydrophobic side chain is free of hydrophilic substituents and cross-linkable functional groups, and wherein the composition is prepared, in a solution, by forming a micelle wherein clusters of the metal are supported by the cross-linkable polymer and then cross-linking the cross-linkable polymer.

2. The composition as in claim 1, wherein the cross-linkable polymer contains a hydrophobic side chain containing an aromatic group, and the micelle is formed by supporting a transition metal by the cross-linkable polymer using a ligand exchange reaction between a transition metal chelate and the aromatic group of the cross-linkable polymer.

3. The composition as in claim 1, wherein the metal clusters are 20 nm or smaller in diameter.

4. The composition as in claim 1, wherein the transition metal is at least one selected from the group consisting of palladium, cobalt, nickel, rhodium, ruthenium, iridium, gold and platinum.

5. The composition as in claim 1, wherein the transition metal is at least one selected from the group consisting of palladium, ruthenium, iridium, gold and platinum.

6. The composition as in claim 1, wherein the transition metal has zero valence.

7. The composition as in claim 1, wherein the cross-linkable polymer contains a hydrophilic side chain having an epoxy group, a carboxyl group, an isocyanate group or a thioisocyanate group.

8. The composition as in claim 7, wherein the cross-linkable polymer further contains at least one type of a hydrophilic side chain having a hydroxyl group, a primary or secondary amino group, or a thiol group.

9. The composition as in claim 1, wherein the cross-linkable polymer is: (i) a polymer or a copolymer obtained by polymerizing or copolymerizing at least one type of A1) monomer having an aromatic group as a hydrophobic side chain, a hydrophilic side chain having a cross-linkable functional group and a polymerizable double bond; or (ii) a copolymer obtained by copolymerizing at least two types of monomers selected from the group consisting of B1) monomer, B2) monomer, and B3) monomer, wherein the B1) monomer is a monomer having an aromatic group as a hydrophobic side chain, a hydrophilic side chain having a cross-linkable functional group and a polymerizable double bond, the B2) monomer is a monomer having an aromatic group as a hydrophobic side chain and a polymerizable double bond, and the B3) monomer is a monomer containing a hydrophilic side chain having a cross-linkable functional group and a polymerizable double bond.

10. The composition as in claim 9, wherein the cross-linkable polymer is a copolymer obtained by copolymerizing at least two types of monomers selected from B1) monomer, B2) monomer, and B3) monomer, wherein the B1) monomer is a monomer represented by chemical formula 1:

wherein $R^1$ is a hydrogen atom or an alkyl group having 1-6 carbon atom(s), $R^2$ is an aryl group having 6-14 carbon atoms, $R^3$ is a covalent bond, an alkylene group having 1-6 carbon atom(s), $-R^9(OR^{10})_m-$, $-R^9(COOR^{10})_n-$ or $R^9(COOR^{10})_o(OR^{10})_p-$, wherein $R^9$ is independently a covalent bond or an alkylene group having 1-6 carbon atom(s), $R^{10}$ is independently an alkylene group having 2-4 carbon atoms, m, n and p are integers of 1-10 and o is 1 or 2, $R^4$ is a carboxyl group, an isocyanate group, an isothiocyanate group, a hydroxyl group, a primary or secondary amino group, a thiol group or a group represented by chemical formula 2:

or chemical formula 3:

wherein $R^5$ is independently an alkylene group having 1-6 carbon atom(s), $R^6$ and $R^7$ are each independently a hydrogen atom or an alkyl group having 1-6 carbon atom(s), and $R^6$ may form a 3-6 membered ring with $R^5$ or $R^7$, the B2) monomer is a monomer represented by chemical formula 4:

wherein $R^1$ and $R^2$ are independently as defined above, $R^{11}$ is a hydrogen atom or an alkyl group having 1-6 carbon atom(s), and the B3) monomer is a monomer represented by chemical formula 5:

wherein $R^1$, $R^3$, $R^4$ and $R^{11}$ are independently as defined above.

11. A method for performing a hydrogenation reaction, a dehydrogenation reaction, an oxidation reaction, an allylic substitution reaction, a coupling reaction or a carbonylation reaction, wherein the method comprises catalyzing the reaction with a composition of claim 1.

12. The composition as in claim 9, wherein the cross-linkable polymer is a polymer obtained by polymerizing one type of A1) monomer represented by chemical formula 1:

wherein $R^1$ is a hydrogen atom or an alkyl group having 1-6 carbon atom(s), $R^2$ is an aryl group having 6-14 carbon atoms, $R^3$ is a covalent bond, an alkylene group having 1-6 carbon atom(s), $-R^9(OR^{10})_m-$, $-R^9(COOR^{10})_n-$ or $R^9(COOR^{10})_o(OR^{10})_p-$, wherein $R^9$ is independently a covalent bond or an alkylene group having 1-6 carbon atom(s), $R^{10}$ is independently an alkylene group having 2-4 carbon atoms, m, n and p are integers of 1-10 and o is 1 or 2, $R^4$ is a carboxyl group, an isocyanate group, an isothiocyanate group, a hydroxyl group, a primary or secondary amino group, a thiol group or a group represented by chemical formula 2:

or chemical formula 3:

wherein $R^5$ is independently an alkylene group having 1-6 carbon atom(s), $R^6$ and $R^7$ are each independently a hydrogen atom or an alkyl group having 1-6 carbon atom(s), and $R^6$ may form a 3-6 membered ring with $R^5$ or $R^7$.

* * * * *